(12) United States Patent
Barlaam et al.

(10) Patent No.: US 7,256,201 B2
(45) Date of Patent: Aug. 14, 2007

(54) SELECTIVE ESTROGEN RECEPTOR-β LIGANDS

(75) Inventors: Bernard Barlaam, Reims (FR); Cathy Dantzman, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 268 days.

(21) Appl. No.: 10/450,023

(22) PCT Filed: Dec. 7, 2001

(86) PCT No.: PCT/SE01/02724

§ 371 (c)(1),
(2), (4) Date: Jun. 6, 2003

(87) PCT Pub. No.: WO02/46164

PCT Pub. Date: Jun. 13, 2002

(65) Prior Publication Data

US 2005/0101584 A1 May 12, 2005

Related U.S. Application Data

(60) Provisional application No. 60/251,779, filed on Dec. 7, 2000, provisional application No. 60/251,775, filed on Dec. 7, 2000.

(30) Foreign Application Priority Data

| Jan. 2, 2001 | (SE) | ................................. | 0100006 |
| Jan. 2, 2001 | (SE) | ................................. | 0100007 |

(51) Int. Cl.
*C07D 217/02* (2006.01)
*A61K 31/47* (2006.01)
(52) U.S. Cl. .................. 514/307; 546/139; 546/144
(58) Field of Classification Search ................ 546/139, 546/144; 514/307
See application file for complete search history.

(56) References Cited

FOREIGN PATENT DOCUMENTS

| EP | 613879 | * | 9/1994 |
| EP | 1113007 A1 | | 7/2001 |
| WO | WO 9621656 A1 | | 7/1996 |
| WO | WO 0062765 A2 | | 10/2000 |
| WO | WO 00/55137 | * | 12/2000 |

OTHER PUBLICATIONS

Chemical Abstracts, vol. 119, Abstract No. 72376, see RN 148234-96-2.*

K. Nagarajan et al., "Antiimplantation Agents: Part IIa—1,2-Diaryl-1,2,3,4-tetrahydroisoquionolines b.c.," Indian Journal of Chemistry, Hindustan CIBA-GEIGY Ltd., Research Centre (Goregaon East, Bombay 400063), p. 83-97, (Jul. 13, 1984).

G. Van Binst et al., "Benzo-and Indoloquinolizine derivatives-VII the dehydrogenation of enamines in quinolizidines," Bull. Soc. Chim. Belg., Laboratorium voor Organische Chasole (Brussel), vol. 85 (No. 1-2), p. 1-9, (Sep. 1, 1976).

Charles K. Bradsher et al., "Schiff Bases as External and Internal Electrophiles in Reactions of Functionalized Organolithium Reagents. A New Route to Isoindoline Derivatives and 1,2,3,4-Tetrahydroisoquinolines 1," J. Org. Chem., Paul M. Gross Chemical Laboratory, Duke University (Durham, North Carolina), vol. 46 (No. 2), p. 327-330, (Aug. 1, 1980).

K. Andrew Hedley et al., "Ring-opening Reactions of N-Aryl-1,2,3,4-tetrahydroisoquinoline Derivatives," Tetrahedron, Pergamon Press plc (Great Britain), vol. 48 (No. 4), p. 743-750, (Nov. 15, 1991).

Rolf Paul et al., "1-Phenyl-2-phenethyl-1,2,3,4-tetrahydroisoquinolines. A New Series of Nonsteroidal Female Antifertility Agents," J. Med. Chem., vol. 15 (No. 7), p. 720-726, (Nov. 2, 1971).

* cited by examiner

*Primary Examiner*—Zinna N. Davis
(74) *Attorney, Agent, or Firm*—White & Case LLP

(57) ABSTRACT

The invention relates to novel compounds having the general formula: (I) and are useful as selective ER-β ligands in the treatment or prophylaxis of Alzheimer's disease, anxiety disorders, depressive disorders, osteoporosis cardiovascular disease, rheumatoid arthritis or prostate cancer.

14 Claims, 2 Drawing Sheets

Alpha      Beta
EC50 2.521e-009   1.159e-009

SELECTIVE ESTROGEN RECEPTOR-β LIGANDS

This application claims the benefit of U.S. Provisional Application No. 60/251,779, filed Dec. 7, 2000 and U.S. Provisional Application No. 60/251,775, filed Dec. 7, 2000.

TECHNICAL FIELD

The present invention is directed to a series of ligands, and more particularly to estrogen receptor-β ligands which have better selectivity than estrogen for the estrogen receptor-β over the estrogen receptor-α, as well as to methods for their production and use in the treatment of diseases related to the estrogen receptor-β, specifically, Alzheimer's disease, anxiety disorders, depressive disorders (including post-partum and post-menopausal depression), osteoporosis, cardiovascular disease, rheumatoid arthritis, or prostate cancer.

BACKGROUND

Estrogen-replacement therapy ("ERT") reduces the incidence of Alzheimer's disease and improves cognitive function in Alzheimer's disease patients (Nikolov et al. Drugs of Today, 34(11), 927-933 (1998)). ERT also exhibits beneficial effects in osteoporosis and cardiovascular disease, and may have anxiolytic and anti-depressant therapeutic properties. However, ERT shows detrimental uterine and breast side effects that limit its use.

The beneficial effects of ERT in post-menopausal human women is echoed by beneficial effects of estrogen in models relevant to cognitive function, anxiety, depression, bone loss, and cardiovascular damage in ovariectomized rats. Estrogen also produces uterine and breast hypertrophy in animal models reminiscent of its mitogenic effects on these tissues in humans.

The beneficial effects of ERT in post-menopausal human women is echoed by beneficial effects of estrogen in models relevant to cognitive function, anxiety, depression, bone loss, and cardiovascular damage in ovariectomized rats. Specifically, experimental studies have demonstrated that estrogen effects the central nervous system ("CNS") by increasing cholinergic function, increasing neurotrophin/neurotrophin receptor expression, altering amyloid precursor protein processing, providing neuroprotection against a variety of insults, and increasing glutamatergic synaptic transmission, among other effects. The overall CNS profile of estrogen effects in pre-clinical studies is consistent with its clinical utility in improving cognitive function and delaying Alzheimer's disease progression. Estrogen also produces mitogenic effects in uterine and breast tissue indicative of its detrimental side effects on these tissues in humans.

The estrogen receptor ("ER") in humans, rats, and mice exists as two subtypes, ER-α and ER-β, which share about a 50% identity in the ligand-binding domain (Kuiper et al. Endocrinology 139(10) 4252-4263 (1998)). The difference in the identity of the subtypes accounts for the fact that some small compounds have been shown to bind preferentially to one subtype over the other (Kuiper et al.).

In rats, ER-β is strongly expressed in brain, bone and vascular epithelium, but weakly expressed in uterus and breast, relative to ER-α. Furthermore, ER-α knockout (ERKO-α) mice are sterile and exhibit little or no evidence of hormone responsiveness of reproductive tissues. In contrast, ER-β knockout (ERKO-β) mice are fertile, and exhibit normal development and function of breast and uterine tissue. These observations suggest that selectively targeting ER-β over ER-α could confer beneficial effects in several important human diseases, such as Alzheimer's disease, anxiety disorders, depressive disorders, osteoporosis, and cardiovascular disease without the liability of reproductive system side effects. Selective effects on ER-β-expressing tissues (CNS, bone, etc.) over uterus and breast could be achieved by agents that selectively interact with ER-β over ER-α.

It is a purpose of this invention to identify ER-β-selective ligands that are useful in treating diseases in which ERT has therapeutic benefits.

It is another purpose of this invention to identify ER-β-selective ligands that mimic the beneficial effects of ERT on brain, bone and cardiovascular function.

It is another purpose of this invention to identify ER-β-selective ligands that increase cognitive function and delay Alzheimer's disease progression.

SUMMARY OF THE INVENTION

This present invention is directed to compounds having the generic structure:

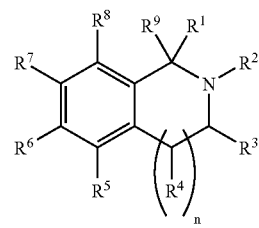

These compounds are ERG-β-selective ligands, which mimic ERT, but lack undesirable side effects of ERT and are useful in the treatment or prophylaxis of Alzheimer's disease, anxiety disorders, depressive disorders, osteoporosis, cardiovascular disease, rheumatoid arthritis or prostate cancer.

These compounds particularly satisfy the formula:

$$(K_{i\alpha A}/K_{i\beta A})/(K_{i\alpha E}/K_{i\beta E}) > 1,$$

preferably:

$$(K_{i\alpha A}/K_{i\beta A})/(K_{i\alpha E}/K_{i\beta E}) > 30,$$

more preferably:

$$(K_{i\alpha A}/K_{i\beta A})/(K_{i\alpha E}/K_{i\beta E}) > 100,$$

wherein $K_{i\alpha A}$ is the $K_i$ value for the ligand in ER-α; $K_{i\beta A}$ is the Ki value for the ligand in ER-β; $K_{i\alpha E}$ is the $K_i$ value for estrogen in ER-α; and $K_{i\beta E}$ is the $K_i$ value for estrogen in ER-β.

DETAILED DESCRIPTION OF THE INVENTION

Figure 1:
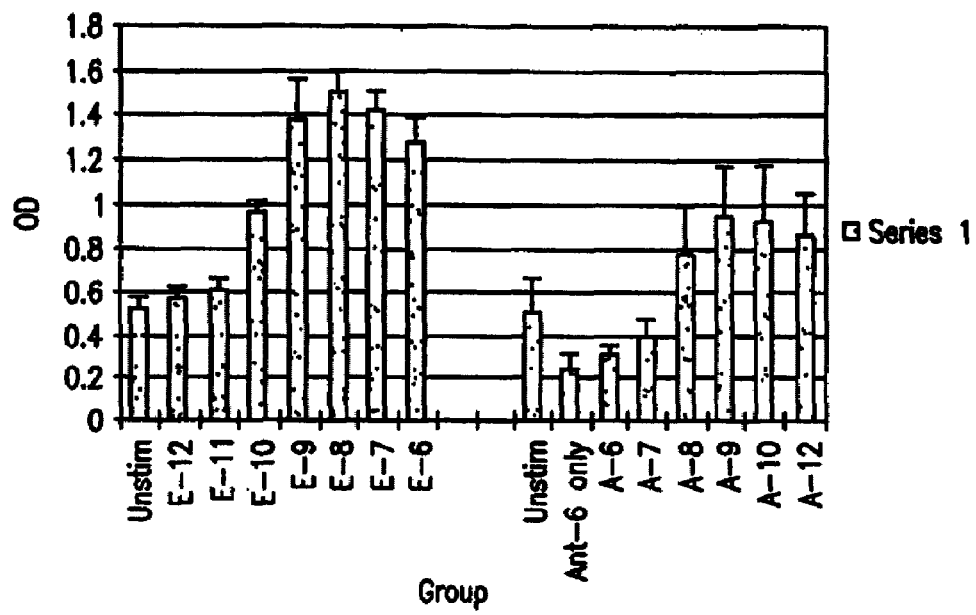
FIG. 1 is a graph of absorbance values obtained in assays for the binding to the estrogen receptor of the ER agonist 17-β-estradiol (E) and the ER antagonist ICI182,780 (A) for cells transfected either with αER or βER.
Figure 1:
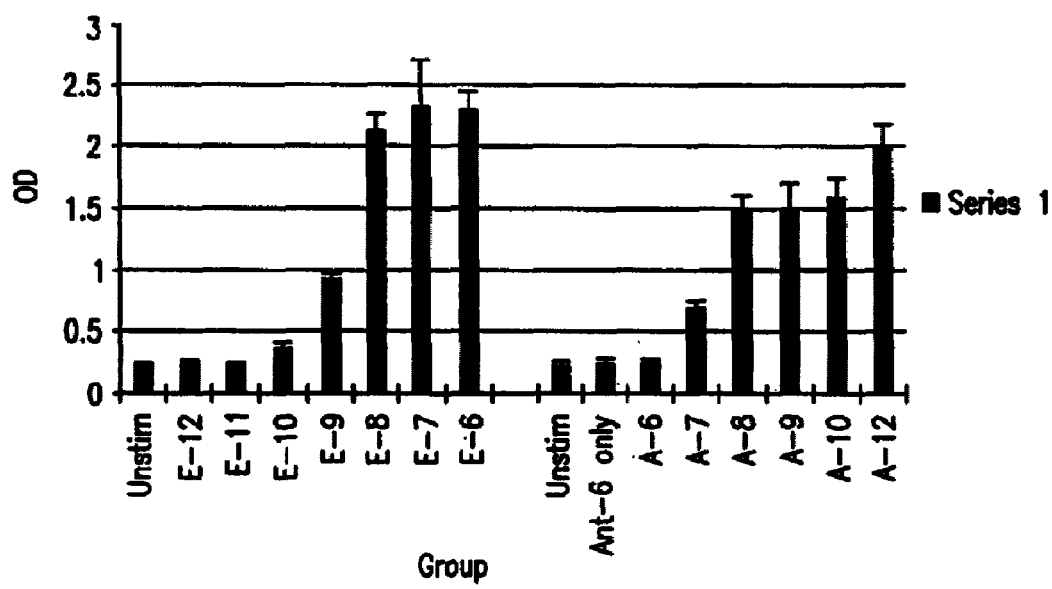

The compounds of the instant invention are ER-β-selective ligands of the structure:

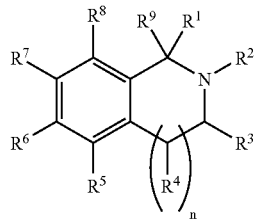

wherein:

$R^1$ is H, $C_{1-8}$alkyl, phenyl, or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$alkyl, phenyl or heterocycle is substituted by 0, 1, 2 or 3 substituents selected from —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl;

$R^2$ is $C_{1-8}$alkyl, phenyl, —C(=O)phenyl, benzyl or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$alkyl, phenyl, —C(=O)phenyl, benzyl or heterocycle is substituted by 1, 2 or 3 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$; —$C(=C)R^a$, —$S(=O)R^a$, —$S(=O)_2R^a$, halogen, cyano, nitro and $C_{1-3}$haloalkyl; and wherein the phenyl, —C(=O)phenyl, benzyl or heterocycle is additionally substituted by 0, 1 or 2 substituents selected from $C_{1-6}$alkyl, phenyl or benzyl;

$R^3$ is hydrogen, $C_{1-6}$alkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings;

$R^4$ is H, halogen, $C_{1-6}$alkyl, $C_{1-6}$haloalkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings;

$R^5$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl; or $R^5$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro;

$R^6$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl;

$R^7$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl;

$R^8$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl; or $R^8$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro;

$R^9$ is H, $C_{1-5}$alkyl or $C_{1-3}$haloalkyl;

$R^a$ is H, $C_{1-6}$alkyl, phenyl or benzyl;

m is 0, 1, 2 or 3; and n is 0 or 1.

In one embodiment of the above compounds, $R^1$ is H, phenyl or a 5- or 6-membered ring heterocycle containing 1, 2 or 3 heteroatoms each independently selected from O, N and S and additionally having 0 or 1 oxo groups and 0 or 1 fused benzo rings, wherein the phenyl or heterocycle is substituted by 0, 1, 2 or 3 substituents selected from —$R^a$, —$OR^a$, —$SR^a$, —$NR^aR^a$, —$OC(=O)R^a$, —$NR^aC(=O)R^a$, —$NR^aS(=O)R^a$, —$NR^aS(=O)_2R^a$, —$S(=O)R^a$, —$S(=O);R^a$, halogen, cyano, nitro and $C_{1-3}$alkyl substituted with 1-7 halogen atoms.

In another embodiment of the above compounds, $R^2$ is phenyl, —C(=O)phenyl, benzyl or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$alkyl, phenyl, benzyl or heterocycle is substituted by 1, 2 or 3 substituents selected from —$OR^a$, —$SR^a$, —$NR^aR^a$, —$OC(=O)R^a$, —$NR^aC(=O)R^a$, —$NR^aS(=O)R^a$, —$NR^aS(=O)_2R^a$, —$S(=O)R^a$, —$S(=O)_2R^a$, halogen, cyano, nitro and $C_{1-3}$haloalkyl; and wherein the phenyl, —C(=O)phenyl, benzyl or heterocycle is additionally substituted by 0, 1 or 2 substituents selected from $C_{1-6}$alkyl, phenyl or benzyl.

In another embodiment of the above compounds, $R^3$ is $C_{1-6}$alkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings.

In another embodiment of the above compounds, $R^4$ is halogen, $C_{1-6}$alkyl, $C_{1-6}$haloalkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings.

In another embodiment of the above compounds, $R^5$ is $C_{1-6}$alkyl, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl; or $R^5$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro.

In another embodiment of the above compounds, $R^6$ is —$R^a$, —$SR^a$, —$NR^aR^a$, —$CO_2R^a$, —$OC(=O)R^a$, —$C(=O)NR^aR^a$, $NR^aC(=O)R^a$, —$NR^aS(=O)R^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl.

In another embodiment of the above compounds, R$^7$ is —OR$^a$, —SR$^a$, —NR$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl.

In another embodiment of the above compounds, R$^8$ is C$_{1-6}$alkyl, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro and C$_{1-3}$haloalkyl; or R$^8$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^8$, halogen, cyano and nitro.

In another embodiment of the above compounds, R$^6$ is OH.

In another embodiment of the above compounds, R$^3$ is H, R$^4$ is H and R$^6$ is OH.

Particularly useful compounds have any of the above embodiments and also satisfy the equation:

$$(K_{i\alpha A}/K_{i\beta A})/(K_{i\alpha E}/K_{i\beta E}) > 100, \text{ wherein}$$

$K_{i\alpha A}$ is the $K_i$ value for the agonist in ER-α;
$K_{i\beta A}$ is the $K_i$ value for the agonist in ER-β;
$K_{i\alpha E}$ is the $K_i$ value for estrogen in ER-α; and
$K_{i\beta E}$ is the $K_i$ value for estrogen in ER-β.

Another aspect of the invention is the use of any of the above compound embodiments for the manufacture of a medicament for the treatment or prophylaxis of Alzheimer's disease, anxiety disorders, depressive disorders, osteoporosis, cardiovascular disease, rheumatoid arthritis or prostate cancer.

Another aspect of the invention is the use of any of the above compound embodiments in the treatment or prophylaxis of Alzheimer's disease, anxiety disorders, depressive disorders (including postpartum and post-menopausal depression), osteoporosis, cardiovascular disease, rheumatoid arthritis or prostate cancer, A pharmaceutical composition comprising:

Another aspect of the invention involves a pharmaceutical composition comprising a therapeutically-effective amount of a compound according to any of the above embodiments and a pharmaceutically-acceptable diluent or carrier.

C$_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "C$_{4-7}$alkyl":

The term "oxo" means a double bonded oxygen (=O).

The compounds of the invention may contain heterocyclic substituents that are 5- or 6-membered ring heterocycles containing 1, 2 or 3 heteroatoms each independently selected from O, N and S and additionally having 0 or 1 oxo groups and 0 or 1 fused benzo rings. A nonexclusive list containing specific examples of such heterocycles are as follows:

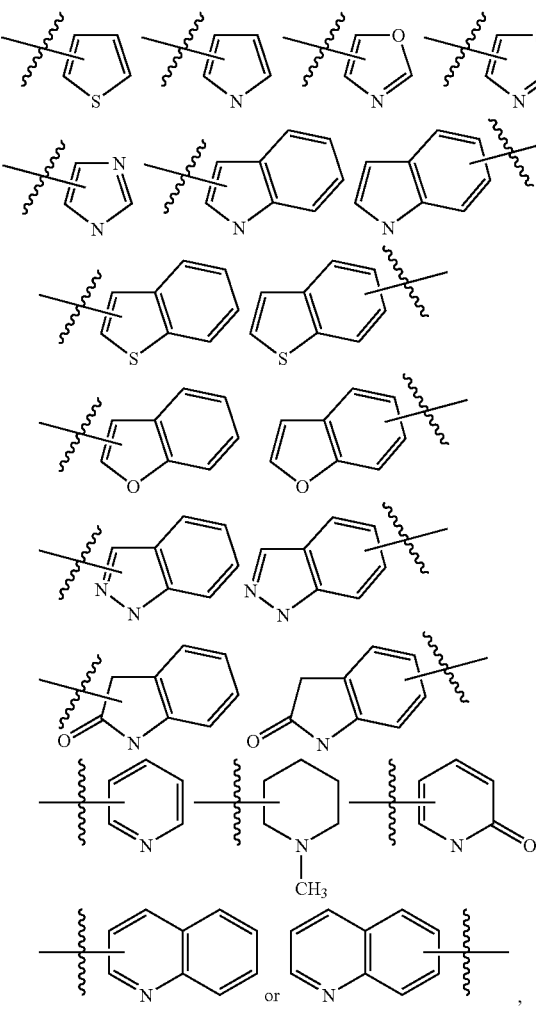

wherein the crossed bond represents that the heterocycle may be attached at any available position on the ring that it contacts.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethyl-sulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

Estrogen Receptor Binding Measurements

Abbreviated Procedure for Fluorescence Polarization Estrogen Receptor (ERFP) Binding Assay A homogeneous mix-and-measure estrogen receptor (ER) binding assay which utilizes fluorescence polarization (FP) technology is used to identify compounds with affinity for the estrogen receptor. Purchased from PanVera (Madison, Wis.), assay reagents include purified human recombinant ERα, human recombinant ERβ, ES2 screening buffer (100 mM potassium phosphate, pH 7.4, 100 μg/mL bovine gamma globulin), and Fluormone™ ES2. Fluormone™ ES2, whose formulation is proprietary to PanVera, is a fluorescein-tagged, estrogen-like molecule which exhibits approximately equal affinity for ERα and ERβ.

For competition binding experiments, dilutions of test compounds are prepared at 2× the final assay concentration in 0.2% DMSO in ES2 Screening buffer on TECAN Genosys, and 25 μL compound/well is dispensed into black Costar ½ volume 96-well plates. Dependent upon a lot specific $K_d$ determination, 10-40 nM ERα or 10-40 nM ERβ and 1 nM Fluormone ES2 are then added to these plates in a final assay volume of 50 μL/well. Plates are gently shaken for at least 5 minutes to mix and incubated for at least 1 hr 45 minutes to achieve equilibrium. (Reaction mixtures are stable for up to 5 hours). After centrifugation to remove air bubbles, plates are read on an LJL Analyst or Acquest equipped with Criterion software at the following settings: Fluorescence Polarization Mode; Static Polarizer on Excitation Side; Dynamic Polarizer on Emission Side; Excitation λ=485×/−5 10 nm; Emission λ=520+/−12.5 nm.

Polarized fluorescence intensity values are collected and subsequently converted electronically to millipolarization (mp) values. Following data reduction and normalization with Excel and/or Prism software, % Ctrl values at the various test concentrations are used to obtain $IC_{50}$ values via non-linear regression analysis of a four-parameter logistic equation.

Because ligand depletion is a consideration in this assay (~40-60% input ES2 is bound in the assay), $IC_{50}$ values are converted to $K_i$ values through application of the Kenakin formula, as outlined in the reference below, rather than via the more routinely-used Cheng-Prusoff formula.

Reference: Bolger et al., Rapid Screening of Environmental Chemicals for Estrogen Receptor Binding Capacity, Environmental Health Perspectives:106 (1998), 1-7.

Cell-Based Assay for ER Transcriptional Activity:

ERs are ligand-dependent transcription factors that bind the promoter regions of genes at a consensus DNA sequence called the estrogen responsive element (ERE). The ER agonist or antagonist activity of a drug was determined by measuring the amount of reporter enzyme activity expressed from a plasmid under the control of an estrogen-responsive element when cells transiently transfected with ER and the reporter plasmid were exposed to drug. These experiments were conducted according to the following methods.

Plasmids:

Estrogen Receptors alpha (αER, Gen Bank accession #M12674), and beta (βER, Gen Bank #X99101 were cloned into the expression vector pSG5 (Stratagene). A trimer of the vitellogenin-gene estrogen response element (vitERE) was synthesized as an oligonucleotide and attached to a beta-globin basal promoter in a construct named pERE3 gal. This response element and promoter were removed from pERE3 gal by digestion with the endonucleases SpeI (filled with Klenow fragment) and HindIII. This blunt/Hind III fragment was cloned into the β-galactosidase (β-gal) enhancer reporter plasmid (pBGALenh, Stratagene). αER and βER plasmids were purified using a the Endo Free Maxi Kit (Qiagen), and the DNA concentration and purity (A260/280 ratio) were determined spectrophotometrically (Pharmacia). Only DNA with A260/280 ratio of 1.8 and a concentration of >1 ug/uL was used for transfections.

Vitellogenin Response Element Sequence:

(SEQ ID NO. 1)
CTAGTCTCGAGAGGTCACTGTGACCTAGATCTAGGTCACTGTGACCTAGATCTAGGTCACTGTGACCTAC

=SpeI overhang
=XhoI site
=AfIII overhang
=ERE consensus
=spacer BgI II

Cells:

All Transfections are performed in 293 cells (Human Embryonic Kidney cells ATCC #CRL-1573). Cells are grown in DMEM supplemented with 10% FBS, glutamine, sodium pyruvate and penicilin/streptomycin. Cells are grown to 70% confluency and split 1:4.

Transfection:

1. 293 cells are split the night before onto collagen I-coated 150 mm tissue-culture plates (Biocoat, Becton Dickinson #354551) at a density of 60-70% in DMEM Mediatech 17-205-CV) 10% charcoal-stripped FBS (biocell #6201-31). Approximately 1×10⁷ cells/plate will yield 70% confluency.

2. The next morning, 1 hour prior to transfection, the media is changed to fresh DMEM 10% FBS stripped and supplements.

3. Transfections are performed using the Profection Kit (Promega #E1200). This kit is based on the calcium-phosphate-mediated transfection technique. Reagents are added in sterile polystyrene tubes in the following order:
Solution A
15 μg αER or βER
45 μg Reporter (pBGALenh or ERE3)
1.5 mL Sterile Water
186 μL $CaCl_2$
*Mix gently
Solution B
1.5 mL 2× Hank's Buffered Salt Solution
4. Using a vortex set on low, add solution A to solution B dropwise. The resulting solution should become milky in color. It is important to achieve thorough mixing. The solution is allowed to settle for 30 minutes, then vortexed before adding the solution to cells.
5. Add the mixture to 150 mm plates dropwise. Mix well by rocking plates back and forth and side to side gently. After an hour, a very fine precipitate should be seen floating on and above cells under 20× magnification. If this precipitate is not observed, the transfection will not be effective. Incubate the cells for 12 hours.

Receptor Stimulation:
1. The day after transfection, cells are washed 2× with calcium- and magnesium-free Mg free PBS containing 1 mM EGTA (pH 7.6). Cells are trypsinized for 2 min with 3 mL of trypsin-EDTA. Trypsin is neutralized with DMEM 10% FCS. Cells are pelleted at 1000×g for 5 min. The cell pellet is then resuspended in 5 mL DMEM plus 2% phenol-red-free FCS supplemented with glutamine, pyruvate, and Penn/Strep.
2. 50 μl of the resulting cell suspension is plated into each well of 96-well tissue culture dishes (Biocoat B&D #354407) using a multi-channel pipettor. The dishes have been previously loaded with 50 μL of DMSO-solubilized test compounds at twice the test concentration in DMEM. Data reported are either n=4 wells (single poke) and n=2 wells (9-point concentration-response curves).
3. Cells are incubated overnight at 37° C. in the selected compounds.

Reporter Assay:
1. After 24 h, 100 μL of 7% CPRG (Roche 0884308) cocktail is added to each well in 1× Z-buffer, the plate is shaken gently at 37° C. for 3 h. CPRG turns bright red as it is cleaved by β-galactosidase.
2. Absorbance measurements (570 nm) were obtained using a plate reader (Molecular Devices).
3. Data is compiled and analyzed using MS Excel.

| 10 × Z Buffer | |
|---|---|
| Sodium Phosphate (dibasic) 1.7 g | 600 mM |
| Sodium Phosphate (monobasic) 0.96 g | 400 mM |
| Potassium Chloride 149 mg | 100 mM |
| Magnesium Sulfate 0.2 mL of 1 molar stock | 100 mM |
| BME 0.78 mL | 500 mM |
| Bring Final Volume to 20 mL with De-Ionized Water | |

7% CPRG COCKTAIL

Figure 2:
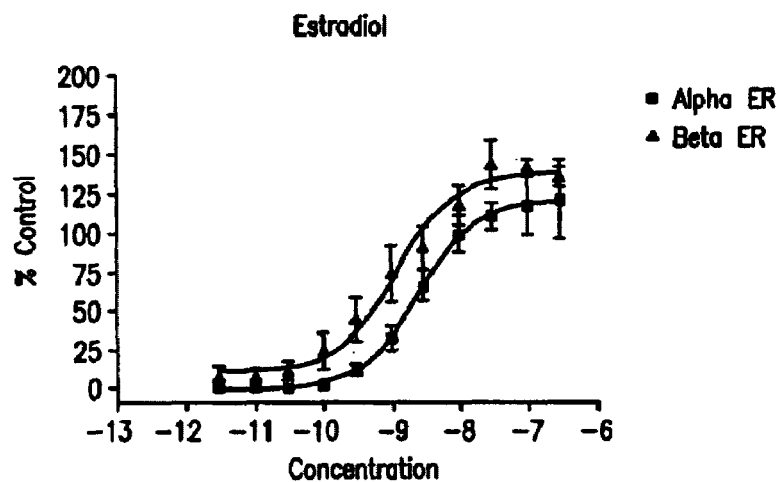
FIG. 2 shows typical concentration-response curves, providing $EC_{50}$ values, for binding to αER and βER.

For 50 mLs:
add 3.5 mL of 50 ml of CPRG
add 3.5 mL of 10× Z Buffer
add 1 mL of 10% SDS
bring to 50 mL with DI water Typical Results:
Absorbance values illustrating typical concentration-response curves obtained for the ER agonist 17-β-estradiol (E) and the ER antagonist ICI182,780 (A) are plotted below for cells transfected with either αER or βER see (FIGS. 1 and 2).

Administration and Use

Compounds of the present invention are shown to have high selectivity for ER-β over ER-α, and may possess agonist activity on ER-β without undesired uterine effects. Thus, these compounds, and compositions containing them, maybe used as therapeutic agents in the treatment of various CNS diseases related to ER-β, such as, for example, Alzheimer's disease.

The present invention also provides compositions comprising an effective amount of compounds of the present invention, including the nontoxic addition salts, amides and esters thereof, which may, serve to provide the above-recited therapeutic benefits. Such compositions may also be provided together with physiologically-tolerable liquid, gel or solid diluents, adjuvants and excipients. The compounds of the present invention may also be combined with other compounds known to be used as therapeutic agents for the above or other indications.

These compounds and compositions may be administered by qualified health care professionals to humans in a manner similar to other therapeutic agents and, additionally, to other mammals for veterinary use, such as with domestic animals. Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders.

In addition to the compounds of the present invention that display ER-β activity, compounds of the present invention can also be employed as intermediates in the synthesis of such useful compounds.

Synthesis

Compounds within the scope of the present invention may be synthesized chemically by means well known in the art. The following Examples are meant to show general synthetic schemes, which may be used to produce many different variations by employing various commercially available starting materials. These Examples are meant only as guides on how to make some compounds within the scope of the invention, and should not be interpreted as limiting the scope of the invention.

EXAMPLES

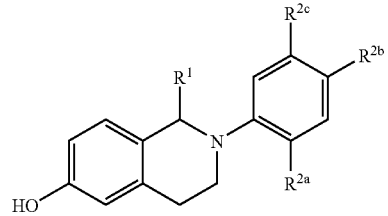

| Example | R¹ | $R^{2a}$ | $R^{2b}$ | $R^{2c}$ |
|---|---|---|---|---|
| 1 | H | H | OH | H |
| 2 | H | Cl | OH | H |
| 3 | H | $CH_3$ | OH | H |
| 4 | H | $OCH_3$ | H | NO2 |
| 5 | H | $NO_2$ | OH | H |
| 6 | phenyl | H | OH | H |
| 7 | 2,4-dimethylphenyl | H | OH | H |
| 8 | 4-methylsulfanylphenyl | H | OH | H |
| 9 | 4-trifluoromethylphenyl | H | OH | H |
| 10 | 2,4-dichlorophenyl | H | OH | H |
| 11 | 4-ethylphenyl | H | OH | H |
| 12 | o-tolyl | H | OH | H |
| 13 | H | Cl | Cl | H |
| 14 | methyl | H | OH | H |
| 15 | ethyl | H | OH | H |
| 16 | benzyl | H | OH | H |
| 17 | methyl | H | H | OH |
| 18 | methyl | $CH_3$ | H | OH |
| 19 | ethyl | H | OH | Cl |
| 20 | phenyl | H | $CH_3$ | OH |
| 21 | 3-furyl | H | $CH_3$ | OH |
| 22 | 2-thiophene | H | $CH_3$ | OH |

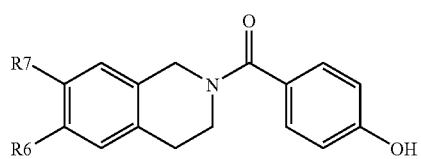

| Example | $R^6$ | $R^7$ |
|---|---|---|
| 23 | OH | H |
| 24 | H | OH |

| Example | Synthetic Method | HPLC (method) | MS | FP β-ER $K_i$ (nM) | FP α-ER $K_i$ (nM) | FP Selectivity |
|---|---|---|---|---|---|---|
| 1 | A, B | 0.46 (A) | 242.0 | 375 | 1000 | 2.7 |
| 2 | A, B | 4.60 (C) | 276.1 | 18 | 48 | 2.7 |
| 3 | A, B | 0.61 (A) | 256.0 | 8 | 60 | 7.4 |
| 4 | A, B | 2.05 (B) | 301.2 | 459 | 655 | 1.4 |
| 5 | A, B | 1.88 (B) | 287.3 | 13 | 62 | 4.8 |
| 6 | C, A, B | 1.58 (A) | 318.4 | 10 | 10 | 0.9 |
| 7 | D, E, B | 1.83 (A) | 346.4 | 35 | 62 | 1.8 |
| 8 | D, E, B | 1.78 (A) | 364.4 | 39 | 18 | 0.5 |
| 9 | D, E, B | 1.58 (A) | 386.4 | 4.9 | 8 | 1.6 |
| 10 | D, E, B | 1.97 (A) | 386.3, 388.3 | 7 | 11 | 1.6 |
| 11 | D, E, B | 1.85 (A) | 346.2 | 9 | 10 | 1.1 |
| 12 | D, E, B | 1.67 (A) | 332.4 | 8 | 16 | 2.2 |
| 13 | A, B | 2.95 (A) | 294.3, 296.3 | 32 | 55 | 1.8 |
| 14 | F, G, H, B | 1.57 (D) | 256.4 | 45 | 307 | 6.8 |
| 15 | G, H, B | 1.74 (D) | 270.4 | 18 | 59 | 3.3 |
| 16 | G, H, B | 2.03 (A) | 332.4 | 18 | 15 | 0.8 |
| 17 | F, G, H, B | 1.44 (D) | 256.2 | 34 | 110 | 3.3 |
| 18 | F, G, H, B | 1.28 (D) | 270.3 | 4.5 | 9 | 2.1 |
| 19 | F, G, H, B | 1.80 (D) | 304.2, 306.2 | 24.4 | 72 | 3.0 |
| 20 | F, G, H, B | 1.89 (D) | 332.5 | 1.2 | 3.0 | 2.5 |
| 21 | F, G, H, B | 1.71 (D) | 322.5 | 3.8 | 22 | 6.0 |
| 22 | F, G, H, B | 2.05 (D) | 338.5 | 3.5 | 12 | 3.5 |
| 23 | I, B | | 270.0 | 229 | 660 | 2.9 |
| 24 | I, B | | 270.2 | 215 | 660 | 3.1 |
| 25 | J, K | | 228 | 55 | 190 | 3.5 |
| 26 | J, K, L | | 256 | 160 | 200 | 1.3 |
| 27 | J, K, L | | 304 | 190 | 170 | 0.9 |

| Example | ERE β-ER $EC_{50}$ (nM) | ERE β-ER Max | ERE α-ER $EC_{50}$ (nM) | ERE α-ER Max | ERE Selectivity |
|---|---|---|---|---|---|
| 1 | | | | | |
| 2 | | | | | |
| 3 | 35.7 | 103 | 28.2 | 93 | 0.8 |
| 4 | | | | | |
| 5 | | | | | |
| 6 | 7.6 | 105 | 0.6 | 100 | 0.1 |
| 7 | | | | | |
| 8 | | | | | |
| 9 | | | | | |
| 10 | | 44 | | 95 | |
| 11 | | | | | |
| 12 | | 71 | | 113 | |
| 13 | | 69 | | 89 | |
| 14 | 143 | 44 | 1000 | 42 | 7.0 |
| 15 | 23 | 51 | 1000 | 37 | 43 |
| 16 | | | | | |
| 17 | 49 | 72 | 2.5 | 87 | 0.1 |
| 18 | 6.1 | 117 | 24.6 | 85 | 4.0 |
| 19 | 209 | 41 | 16.8 | 66 | 0.1 |
| 20 | 0.4 | 85 | 1.2 | 75 | 3.3 |
| 21 | 0.7 | 106 | 0.8 | 77 | 1.1 |
| 22 | | | | | |
| 23 | | | | | |
| 24 | | | | | |
| 25 | 161 | 77 | 192 | 60 | 1.2 |
| 26 | 79 | 85 | 73 | 102 | 0.9 |
| 27 | 34 | 90 | 6.8 | 54 | 0.2 |

HPLC conditions used:
HPLC Method A: This method was used unless otherwise stated. 50 × 2.1 mm, Zorbax Stablebond $C_8$ column; flow rate 1.4 mL/min, linear gradient from 15% B to 90% B over 4 min; A = water, 0.05% TFA; B = 90% $CH_3CN$, 10% water, 0.05% TFA; UV detection at 215 nm.
HPLC Method B:
The same method as for A, except UV detection 254 nm.
HPLC Method C: 75 × 4.60 mm, 3 mm, $C_{18}$ Phenomenex-Luma column; flow rate 1.0 mL/min, linear gradient from 20% B to 80% B over 10 min; A = water, 0.1% TFA; B = $CH_3CN$, 0.1% TFA; UV detection at 210 and 254 nm.
HPLC Method D: 50 × 2.1 mm, Zorbax Stablebond $C_8$ column; flow rate 1.4 mL/min, linear gradient from 5% B to 90% B over 4 min; A = water, 0.05% TFA; B = 90% $CH_3CN$, 10% water, 0.05% TFA; DAD detection.
$CH_3CN$: acetonitrile
TFA: trifluoroacetic acid
DMSO: dimethylsulfoxide
$CH_2Cl_2$: methylene chloride Example 1

2-(4-Hydroxyphenyl)-1,2,3,4-tetrahydroisoquinoline-6-ol

1) Synthetic Method A: Synthesis of 6-methoxy-2-(4-methoxyphenyl)-1,2,3,4-tetrahydroisoquinoline A solution of 6-methoxy-1,2,3,4-tetrahydroisoquinoline [1] (0.130 g) in toluene (1.75 mL) was added to sodium t-butoxide (0.092 g) in a 5 mL reaction vial equipped with a frit. A suspension of tris(dibenzylideneacetone) dipalladium (0) (0.022 g) and (R)-(+)-2,2'-bis(diphenylphosphino)-1,1'-binaphthyl (0.040 g) in toluene (0.75 mL) was added to the above mixture. The reaction was agitated at 80° C. for 18 h, then cooled and the solids were removed by filtering the reaction through the frit. The filtrate was evaporated and the resulting residue was purified by chromatography on silica gel (eluant: ethylacetate-hexane, gradient from 5:95 to 1:1) to give the title compound (0.065 g). MS: 270.1 (MH$^+$); TLC R$_f$: 0.33 (20% ethyl acetate hexane); $^1$H NMR (DMSO-d$_6$): 7.04 (d, 1H, J=8.4 Hz), 6.97 (d, 2H, J=9.2 Hz), 6.86 (d, 2H, J=9.1 Hz), 6.75 (dd, 1H, J=2.6, 8.4 Hz), 6.68 (d, 1H, J=2.5 Hz), 4.24 (s, 2H), 3.79 (s, 3H), 3.78 (s, 3H), 3.43 (t, 2H, J=5.8 Hz), 2.96 (t, 2H, J=5.7 Hz).

Reference 1: made according to J. S. Buck, *J. Am. Chem. Soc.*; 1934; 56; 1769.

2) Synthetic Method B: Synthesis of 2-(4-hydroxyphenyl)-1,2,3,4-tetrahydroisoquinoline-6-ol A 1.0 M solution of boron tribromide in CH$_2$Cl$_2$ (0.54 mL) was added dropwise to a cooled (−15° C.) solution of 6-methoxy-2-(4-methoxyphenyl)-1,2,3,4-tetrahydroisoquinoline (0.036 g) in CH$_2$Cl$_2$ (1.4 mL). After 30 min the reaction was warmed to room temperature. After 2 h the reaction was diluted with CH$_2$Cl$_2$ (30 mL) and washed successively with saturated aqueous sodium bicarbonate (2×20 mL) and saturated aqueous sodium chloride (1×15 mL). The organic extract was dried and evaporated. The resulting residue was purified by chromatography on silica gel (eluant; a gradient of 0 to 20% methanol in dichloromethane) to give the title compound (0.026 g); MS: 242.0 (MH$^+$); HPLC t$_R$: 0.46 min; $^1$H NMR (DMSO-d$_6$): 9.14 (s, 1H), 8.79 (s, 1H), 6.94 (d, 1H, J=6 Hz), 6.85 (d, 2H, J=6.65 (d, 2H J=9 Hz), 6.56 (d, 1H, J=6 Hz), 6.52 (s, 1H), 4.06.(s, 2H), 3.28 (t, 2H, J=6 Hz), 2.78 (t, 2H, J=6 Hz).

Example 2

2-(2-Chloro-4hydroxyphenyl)-1,2,3,4-tetrahydroisoquinoline-6-ol

According to synthetic methods A and B, from 4-bromo-3-chloroanisole (0.150 g) was obtained 2-(2-chloro-4-methoxyphenyl)-6-methoxy-1,2,3,4-tetrahydroisoquinoline (0.057 g) after purification by chromatography on silica gel (eluant: ethyl acetate-hexane, gradient from 5:95 to 1:1); MS: 304.2 (100%) (MH$^+$), 306.2 (40%) (MH$^+$); TLC R$_f$: 0.47 (20% ethyl acetate:hexane); and 2-(2-chloro-4-hydroxyphenyl)-1,2,3,4-tetrahydroisoquinoline-6-ol (0.044 g) was obtained after purification by chromatography on silica gel (eluant: a gradient of 0 to 4% methanol in dichloromethane); MS: 276.1 (MH$^+$); HPLC t$_R$: 4.60 min (method C); $^1$H NMR (MeOD-d$_4$): 7.06 (d, 1H, J=8.7 Hz), 6.90 (d, 1H, J=7.8 Hz), 6.85 (d, 1H, J=2.7 Hz), 6.69 (dd, 1H, J=8.9, 2.9 Hz), 6.60 (d, 1H, J=2.7 Hz), 6.57 (s, 1H), 4.01 (s, 2H), 3.19 (t, 2H, J=5.7 Hz), 2.90 (t, 2H, J=5.7 Hz).

Example 3

2-(4-Hydroxy-2-methylphenyl)-1,2,3,4-tetrahydroisoquinolin-6-ol

According to synthetic methods A and B, from 2-bromo-5-methoxytoluene (0.15 mL) was obtained 6-methoxy-2-(4-methoxy-2-methylphenyl)-1,2,3,4-tetrahydroisoquinoline (0.188 g) after purification by chromatography on silica gel (eluant: ethyl acetate-hexane, gradient from 5:95 to 1:1); MS: 284.1 (MH$^+$); TLC R$_f$=0.64 (20% ethyl acetate:hexane); and using the compound isolated above (0.094 g), the title compound (0.061 g) was obtained after purification by silica gel chromatography (eluant: a gradient from 0 to 20% methanol in CH$_2$Cl$_2$); MS: 256.0 (MH$^+$; HPLC t$_R$: 0.61 min; $^1$H NMR (DMSO-d$_6$): 9.12 (s, 1H), 8.97 (s, 1H), 6.93 (d, 1H, J=8.4 Hz), 6.87 (d, 1H, J=8.7 Hz), 6.53-6.60 (m, 4H), 3.81 (s, 2H), 2.95-2.97 (m, 2H), 2.81-2.82 (m, 2H).

Example 4

2-(2-Methoxy-5-nitrophenyl)-1,2,3,4-tetrahydroisoquinolin-6-ol

According to synthetic method A, from 2-bromo-4-nitroanisole (0.222 g) was obtained 6-methoxy-2-(2-methoxy-5-nitrophenyl)-1,2,3,4-tetrahydroisoquinoline (0.068 g) after purification by chromatography on silica gel (eluant: ethyl acetate-hexane, gradient from 5:95 to 1:1); MS: 315.1 (MH$^+$); TLC R$_f$: 0.28 (20% ethyl acetate; hexane). 2-(2-Methoxy-5-nitrophenyl)-1,2,3,4tetrahydroisoquinolin-6-ol (0.033 g) was obtained when the above isolated compound was treated with 1.2 equivalents of 1.0 M boron tribromide according to synthetic method B and after purification by silica gel chromatography (eluant: a gradient from 0 to 7% methanol in CH$_2$Cl$_2$); MS: 301.2 (MH$^+$); HPLC t$_R$: 2.05 min (method B); $^1$H NMR (DMSO-d$_6$): 9.14 (s, 1H), 7.92 (dd, 1H, J=2.7, 9.0 Hz), 7.72 (d, 1H, J=2.7 Hz), 7.17 (d, 1H, J=9.0 Hz), 6.97 (d, 1H, J=8.1 Hz), 6.59 (dd, 1H, J=2.3, 8.1 Hz), 6.55 (s, 1H), 4.15 (s, 2H), 3.96 (s, 3H), 3.33 (t, 2H, J=5.6 Hz), 2.82 (t, 2H, J=5.5 Hz).

Example 5

2-(4-Hydroxy-2-nitrophenyl)-1,2,3,4-tetrahydroisoquinolin-6-ol

According to synthetic method A, from 4-bromo-3-nitroanisole (0.222 g) was obtained 6-methoxy-2-(4-methoxy-2-nitrophenyl)-1,2,3,4-tetrahydroisoquinoline (0.057 g) after purification by chromatography on silica gel (eluant: ethyl acetate-hexane, gradient from 5:95 to 1:1); MS: 315.1 (MH$^+$); TLC R$_f$: 0.32 (20% ethyl acetate hexane). According to synthetic method B, from the above isolated compound the title compound (0.008 g) was obtained after purification by chromatography on silica gel (eluant: a gradient of 0 to 7% methanol in dichloromethane); MS: 287.3 (MH$^+$; HPLC t$_R$: 1.88 min (method B); $^1$H NMR (DMSO-d$_6$+TFA-d): 7.46 (d, 1H, J=9.0 Hz), 7.24 (d, 1H, J=2.7 Hz), 7.11 (dd, 1H, J=6.0, 3.0 Hz), 6.92 (d, 1H, J=8.1 Hz), 6.60-6.64 (m, 2H), 4.14 (s, 2H), 3.26 (t, 2H, J=5.7 Hz), 2.87 (t, 2H, J=5.7 Hz).

Example 6

2-(4Hydroxyphenyl)-1-phenyl-1,2,3,4-tetrahydroisoquinolin-6-ol

1) Synthetic Method C: Synthesis of 6-methoxy-1-phenyl-1,2,3,4-tetrahydroisoquinoline 3-Methoxyphenylethylamine (1.5 g) and benzaldehyde (1.0 mL) were reacted together in benzene (10 mL) in a modified Dean-Stark apparatus, where the side arm contained activated 3 Å molecular sieve beads. The reaction was vigorously refluxed for 1 h until a uniform solution resulted. The reaction was cooled and evaporated. The resulting residue was taken up in trifluoroacetic acid (6 mL) and heated to 60° C. for 18 h. The reaction was cooled, concentrated then partitioned between 1N sodium hydroxide (70 mL) and diethyl ether (50 mL). The organic layer was washed with 0.5 N sodium hydroxide (70 mL), dried, concentrated to 20 mL and cooled in an ice-water bath. The crystals that formed were collected and dried to give the title compound (1.90 g). MS: 240.0 (MH$^+$); HPLC $t_R$: 1.62 min (method D); $^1$H NMR (DMSO-d$_6$+TFA-d): 7.47-7.49 (m, 3H), 7.37-7.39 (m, 2H), 6.90 (broad s, 1H), 6.79 (dd, 1H, J=2.4, 8.7 Hz), 6.66 (d, 1H, J=8.7 Hz), 5.75 (s, 1H), 3.77 (s, 3H), 3.39-3.44 (m, 2H), 3.17-3.28 (m, 1H), 3.04-3.12 (m, 1H).

2) Synthesis of 2-(4-hydroxyphenyl)-1-phenyl-1,2,3,4-tetrahydroisoquinolin-6-ol

According to synthetic method A, from 4-bromoanisole (0.17 mL) was obtained 6-methoxy-2-(4-methoxy-phenyl)-1-phenyl-1,2,3,4-tetrahydroisoquinoline (0.045 g) after purification by chromatography on silica gel (eluant: ethyl acetate-hexane, gradient from 5:95 to 1:1); MS: 346.3 (MH$^+$); HPLC $t_R$: 2.24 min; TLC R$_f$=0.20 (5% ethyl acetate:hexane). According to synthetic method B, from the above isolated compound the title compound (0.034 g) was obtained after purification by silica gel chromatography (eluant: a gradient of 0 to 20% methanol in dichloromethane); MS: 318.4 (MH$^+$); HPLC $t_R$: 1.58 min; TLC R$_f$: 0.30 (5% methanol; CH$_2$Cl$_2$); $^1$H NMR (DMSO-d$_6$): 9.20 (s, 1H), 8.64 (s, 1H), 7.12-7.20 (m, 5H), 6.94 (d, 1H, J=7.8 Hz), 6.69 (d, 2H, J=8.8 Hz), 6.54-6.59 (m, 4H), 5.58 (s, 1H), 3.35-3.45 (m, 2H), 2.81 (t, 2H, J=5.8 Hz).

Example 7

1-(2,4-Dimethylphenyl)-2-(4-hydroxyphenyl)-1,2,3,4-tetrahydroisoquinolin-6-ol

1) Synthetic method D: Synthesis of 1-(2,4-dimethylphenyl)-6-methoxy-1,2,3,4-tetrahydroisoquinoline 3-Methoxyphenylethylamine (1.51 g) and 2,4-dimethylbenzaldehyde (1.34 g) were mixed together. Phosphoric acid, 85%, (20 mL) was added then the reaction was warmed to 37° C. for 60 h. The reaction was cooled, poured into water (300 mL) then washed with diethyl ether (2×50 mL). The aqueous layer was diluted to 700 mL with water, made basic (pH=10) by the slow addition of sodium hydroxide, and then extracted with diethyl ether (2×150 mL). The organic extracts were dried and evaporated. The resulting residue was purified by silica gel chromatography (eluant: ethyl acetate-hexane, gradient from 1:1 to 100% ethyl acetate) to give the title compound (1.458 g). MS: 268.2 (MH$^+$); HPLC $t_R$: 1.71 min (method D); TLC R$_f$: 0.21 (ethyl acetate); $^1$H NMR (DMSO-d$_6$): 6.96 (s, 1H), 6.86 (s, 2H), 6.67 (d, 1H, J=2.3 Hz), 6.59 (dd, 1H, J=2.5, 8.5 Hz), 6.44 (d, 1H, J=8.5 Hz), 5.07 (s, 1H), 3.69 (s, 3H), 3.03-3.11 (m, 1H), 2.82-2.89 (m, 2H), 2.63-2.77 (m, 1H), 2.26 (s, 3H), 2.23 (s, 3H).

2) Synthetic Method E: Synthesis of 1-(2,4-dimethylphenyl)-6-methoxy-2-(4-methoxyphenyl)-1,2,3,4-tetrahydroisoquinoline A fine suspension of sodium t-butoxide (0.055 g) and 4-bromoanisole (0.112 g) in toluene (4.66 mL) was added to 1-(2,4-dimethylphenyl)-6-methoxy-1,2,3,4-tetrahydroisoquinoline (0.134 g) in a 10 mL reaction vial equipped with a frit. A solution of tris(dibenzylideneacetone) dipalladium (0) (2.52 µmol) and 2-dicyclohexylphosphino-2'-((N,N)-dimethylamino)-biphenyl [2] (5.9 mg) in toluene (0.90 mL) was added. The reaction was agitated at 95° C. for 34 h, then cooled and the solids were removed by filtering the reaction through the frit. The filtrate was evaporated and the resulting residue was purified by chromatography on silica gel (eluant: a gradient from 0 to 20% ethyl acetate in hexane) to give the title compound (0.054 g). MS: 374.5 (MH$^+$); HPLC $t_R$: 2.40 min; TLC R$_f$: 0.61 (20% ethyl acetate:hexane).

Reference 2: made according to D. W. Old, J. P. Wolfe, S. L. Buchwald, *J. Am. Chem. Soc.*; 1998; 120; 9722-9723.

3) Synthesis of 1-(2,4-Dimethylphenyl)-2-(4-hydroxyphenyl)-1,2,3,4-tetrahydroisoquinolin-6-ol According to synthetic method B, from 1-(2,4-dimethylphenyl)-6-methoxy-2-(4-methoxyphenyl)-1,2,3,4-tetrahydroisoquinoline (0.050 g) was obtained the title compound (0.023 g) after silica gel chromatography (eluant: a gradient of 0 to 12% methanol in dichloromethane); MS: 346.4 (MH$^+$); HPLC $t_R$: 1.83 min; $^1$H NMR (DMSO-d$_6$): 9.16 (s, 1H), 8.79 (s, 1H), 6.89 (s, 1H), 6.79-6.84 (m, 2H), 6.51-6.66 (m, 7H), 5.54 (s, 1H), 3.15-3.23 (m, 2H), 2.66 (broad s, 2H), 2.20 (s, 6H).

Example 8

2-(4-Hydroxyphenyl)-1-(4-methylsulfanylphenyl)-1,2,3,4-tetrahydroisoquinolin-6-ol According to synthetic method D using 4-(methylthio)benzaldehyde (1.33 mL), 3-methoxy-1-(4-methylsulfanylphenyl)-1,2,3,4-tetrahydroisoquinoline (0.441 g) was obtained after silica gel chromatography (eluant: ethyl acetate-hexane, gradient from 1:1 to 100% ethyl acetate). MS: 286.2 (MH$^+$); HPLC $t_R$: 1.65 min (method D); TLC R$_f$: 0.11 (ethyl acetate); $^1$H NMR (DMSO-d$_6$): 7.18 (s, 4H), 6.67 (d, 1H, J=2.2 Hz), 6.59 (dd, 1H, J=2.4, 8.4 Hz), 6.52 (d, 1H, J=8.4 Hz), 4.88 (s, 1H), 3.69 (s, 3H), 3.02-3.07 (m, 1H), 2.82-2.88 (m, 2H), 2.66-2.71 (m, 1H), 2.45 (s, 3H). According to synthetic method E using the above isolated compound (0.143 g), 6-methoxy-2-(4-methoxyphenyl)-1-(4-methylsulfanylphenyl)-1,2,3,4-tetrahydroisoquinoline (0.052 g) was obtained after silica gel chromatography (eluant: a gradient from 0 to 20% ethyl acetate in hexane); MS: 392.5 (MH$^+$), HPLC $t_R$: 2.37 min; TLC R$_f$: 0.47 (20% ethyl acetate:hexane). According to synthetic method B using the above isolated compound (0.047 g), the title compound (0.034 g) was obtained after silica gel chromatography (eluant: a gradient of 0 to 12% methanol in dichloromethane); MS: 364.4 (MH$^+$); HPLC $t_R$: 1.78 min; $^1$H NMR (DMSO-d$_6$): 9.23 (s, 1H), 8.69 (s, 1H), 7.07-7.08 (m, 4H), 6.91 (d, 1H, J=7.5 Hz), 6.69-6.72 (m, 2H), 6.56-6.59 (m, 4H), 5.55 (s, 1H), 2.81 (broad s, 2H), 2.50 (broad s, 2H), 2.40 (s, 3H).

Example 9

2-(4-Hydroxyphenyl)-1-(4-trifluoromethylphenyl)-1,2,3,4-tetrahydroisoquinolin-6-ol According to synthetic method D using 4-(trifluoromethyl)benzaldehyde, (1.74 g), 6-methoxy-1-(4-trifluoromethylphenyl)-1,2,3,4-tetrahydroisoquinoline (1.208 g) was obtained after silica gel chromatography (eluant: ethyl acetate-hexane, gradient from 1:1 to 100% ethyl acetate); MS: 308.2 (MH$^+$); HPLC $t_R$: 1.93 min; TLC $R_f$: 0.32 (ethyl acetate). According to synthetic method E using the above isolated compound (0.154 g), 6-methoxy-2-(4-methoxyphenyl)-1-(4-trifluoromethylphenyl)-1,2,3,4-tetrahydroisoquinoline (0.063 g) was obtained after silica gel chromatography (eluant: a gradient from 0 to 20% ethyl acetate in hexane); MS: 414.4 (MH$^+$); HPLC $t_R$: 2.78 min; TLC $R_f$: 0.41 (20% ethyl acetate: hexane). According to synthetic method B using the above isolated compound, the title compound (0.057 g) was obtained after silica gel chromatography (eluant: a gradient of 0 to 8% methanol in dichloromethane); MS: 386.4 (MH$^+$); HPLC $t_R$: 1.58 min; $^1$H NMR (DMSO-d$_6$): 9.29 (s, 1H), 8.72 (s, 1H), 7.58 (d, 2H, J=7.9 Hz), 7.37 (d, 2H, J=7.9 Hz), 6.97 (d, 1H, J=7.9 Hz), 6.69-6.73 (m, 2H), 6.56-6.60 (m, 4H), 5.70 (s, 1H), 3.39-3.45 (m, 1H), 3.25-3.28 (m, 1H), 2.83 (broad s, 2H).

Example 10

1-(2,4-Dichlorophenyl)-2-(4-hydroxyphenyl)-1,2,3,4-tetrahydroisoquinolin-6-ol

According to synthetic method D using 2,4-dichlorobenzaldehyde (1.75 g), 1-(2,4-dichlorophenyl)-6-methoxy-1,2,3,4-tetrahydroisoquinoline (0.241 g) was obtained after silica gel chromatography (eluant; ethyl acetate-hexane, gradient from 1:1 to 100% ethyl acetate); MS: 308.3 (100%) (MH$^+$), 310.4 (60%) (MH$^+$); HPLC $t_R$: 1.87 min; TLC $R_f$: 0.58 (ethyl acetate-hexane 1:1). According to synthetic method B using the above isolated compound (0.154 g), 1-(2,4-dichlorophenyl)-6-methoxy-2-(4-methoxyphenyl)-1,2,3,4-tetrahydroisoquinoline (0.075 g) was obtained after silica gel chromatography (eluant; a gradient from 0 to 20% ethyl acetate in hexane); MS: 414.4 (100%) (MH$^+$), 416.4 (50%) (MH$^+$); HPLC $t_R$: 2.95 min; TLC $R_f$: 0.59 (20% ethyl acetate:hexane). According to synthetic method B using the above isolated compound, the title compound (0.062 g) was obtained after silica gel chromatography (eluant: a gradient of 0 to 8% methanol in dichloromethane); MS: 386.3 (100%), 388.3 (60%) (MH$^+$); HPLC $t_R$: 1.97 min; $^1$H NMR (DMSO-d$_6$): 9.30 (s, 1H), 8.88 (s, 1H), 7.52 (s, 1H), 7.26 (d, 1H, J=8.1 Hz), 7.08 (d, 1H, J=8.4 Hz), 6.82 (d, 2H, J=8.4 Hz), 6.70 (d, 1H, J=8.2 Hz), 6.52-6.59 (m, 4H), 5.78 (s, 1H), 3.27-3.35 (m, 2H), 2.87-2.92 (m, 1H), 2.71-2.76 (m, 1H).

Example 11

1-(4-Ethylphenyl)-2-(4-hydroxyphenyl)-1,2,3,4-tetrahydroisoquinolin-6-ol

According to synthetic method D using 4-ethylbenzaldehyde (1.37 mL), 1-(4-ethylphenyl)-6-methoxy-1,2,3,4-tetrahydroisoquinoline (0.977 g) was obtained after silica gel chromatography (eluant: ethyl acetate-hexane, gradient from 1:1 to 100% ethyl acetate); MS: 268.3 (MH$^+$); HPLC $t_R$: 1.80 min (method D); TLC $R_f$: 0.15 (ethyl acetate). According to synthetic method E using the above isolated compound (0.134 g), 1-(4-ethylphenyl)-6-methoxy-2-(4-methoxyphenyl)-1,2,3,4-tetrahydroisoquinoline (0.055 g) was obtained after silica gel chromatography (eluant: a gradient from 0 to 20% ethyl acetate in hexane); MS: 374.5 (MH$^+$); HPLC $t_R$: 2.45 min; TLC $R_f$: 0.57 (20% ethyl acetate:hexane). According to synthetic method B using the above isolated compound, the title compound (0.045 g) was obtained after silica gel chromatography (eluant: a gradient of 0 to 12% methanol in dichloromethane); MS: 346.2 ; (MH$^+$); HPLC $t_R$: 1.85 min.

Example 12

2-(4-Hydroxyphenyl)-1-o-tolyl-1,2,3,4-tetrahydroisoquinolin-6-ol

According to synthetic method D using o-toluadlehyde (1.16 mL), 6-methoxy-1-o-tolyl-1,2,3,4-tetrahydroisoquinoline (1.072 g) was obtained after silica gel chromatography (eluant: ethyl acetate-hexane, gradient from 1:1 to 100% ethyl acetate); MS: 254.3 (MH$^+$); HPLC $t_R$: 1.67 min; TLC $R_f$: 0.28 (ethyl acetate-hexane 1:1). According to synthetic method E using the above isolated compound (0.127 g), 6-methoxy-2-(4-methoxy-phenyl)-1-o-tolyl-1,2,3,4-tetrahydroisoquinoline (0.062 g) was obtained after silica gel chromatography (eluant: a gradient from 0 to 20% ethyl acetate in hexane); MS: 360.5 (MH$^+$); HPLC $t_R$: 2.26 min; TLC $R_f$: 0.46 (20% ethyl acetate:hexane). According to synthetic method B using the above isolated compound, the title compound (0.044 g) was obtained after silica gel chromatography (eluant: a gradient of 0 to 12% methanol in dichlioromethane); MS: 332.4 (MH$^+$); HPLC $t_R$: 1.67 min.

Example 13

2-(2,4-Dichloro-phenyl)-1,2,3,4-tetrahydro-isoquinolin-6-ol

According to synthetic methods A and B, from 1-bromo-2,4-dichloro-benzene (0.25 g) was obtained 2-(2,4-dichloro-phenyl)-6-methoxy-1,2,3,4-tetrahydro-isoquinoline (0.092 g) after purification by chromatography on silica gel (eluant: ethyl acetate-hexane, gradient from 5:95 to 1:1); MS: 306.3, 308.3, 310.3 (MH$^+$); HPLC $t_R$: 1.67 min; TLC $R_f$=0.72 (20% ethyl acetate:hexane); and using the compound isolated above (0.092 g), the title compound (0.034 g) was obtained after purification by silica gel chromatography (eluant: a gradient from 0 to 5% methanol in CH$_2$Cl$_2$); MS: 294.3, 296.3 (MH$^+$); HPLC $t_R$: 2.95 min; TLC $R_f$=0.53 (5% methanol:methylene chloride).

Example 14

2-(4-Hydroxy-phenyl)-1-methyl-1,2,3,4-tetrahydro-isoquinolin-6-ol

1) Synthetic Method F: Synthesis of (4-methoxy-phenyl)-[2-(3-methoxy-phenyl)-ethyl]-amine A solution of (3-methoxy-phenyl)-acetyl chloride (5.0 g) in ethyl acetate (85 mL) was added to a solution of 4methoxy-phenylamine (3.33 g) in ethyl acetate (50 mL). After 18 h the reaction was poured into water (150 mL). The organic extract was dried over sodium sulfate, filtered through celite and concentrated. The resulting residue was dissolved in tetrahydrofurane (100 mL) then lithium aluminum hydride (5.2 g) was added in small portions over 30 minutes. After 18 h the reaction was slowly poured onto 200 mL of ice. The mixture was filtered through a pad of celite and the collected filtrate was extracted with ethyl acetate (300 mL). The organic extract was dried over sodium sulfate, filtered through celite and concentrated to give the title compound. MS: 258.3 (MH$^+$); HPLC $t_R$: 1.98 min.

2) Synthetic Method G: Synthesis of N-(4-methoxy-phenyl)-N-[2-(3-methoxy-phenyl)-ethyl]-acetamide (4-Methoxy-phenyl)-[2-(3-methoxy-phenyl)-ethyl]-amine (3.87 mmol) and acetyl chloride (4.26 mmol) were reacted ethyl acetate (50 mL). After 18 hours, the reaction was poured into ice (150 mL) and the organic extract was dried over sodium sulfate, filtered through celite and concentrated. The title compound (0.60 g) was obtained after silica gel chromatography (eluant: gradient from 10% to 40% ethyl acetate-hexane); MS: 300.4 (MH$^+$); HPLC $t_R$: 2.65 min; TLC $R_f$: 0.19 (ethyl acetate-hexane 2:3).

3) Synthetic Method H: Synthesis of 6-methoxy-2-(4-methoxy-phenyl)-1-methyl-1,2,3,4-tetrahydro-isoquinoline N-(4-Methoxy-phenyl)-N-[2-(3-methoxyphenyl)-ethyl]-acetamide (0.60 g) was heated to 80° C. in phosphorus oxychloride (8.4 mL) for 24 h. The reaction was cooled then poured slowly onto ice (150 mL). Potassium iodide (0.65 g) was added. After 30 min, the mixture was extracted with methylene chloride (2×50 mL). The organic extracts were dried over sodium sulfate, filtered through celite and concentrated. The resulting residue was dissolved in methanol (21 mL) and sodium borohydride (0.23 g) was added slowly in small portions. After 18 h the solvent was removed under reduced pressure. The residue was partitioned between water (100 mL) and ethyl acetate (50 mL) and the aqueous layer was extracted with ethyl acetate (25 mL). The combined organic extracts were dried over sodium sulfate, filtered through celite and concentrated giving the title compound MS: 284.3 (MH$^+$); HPLC $t_R$; 2.11 min (method D).

According to synthetic method B, 2-(4-hydroxy-phenyl)-1-methyl-1,2,3,4-tetrahydro-isoquinolin-6-ol was obtained (0.085 g) after purification by chromatography on silica gel (eluant: a gradient of 0 to 4% methanol in dichloromethane); MS: 256.4 (MH$^+$); HPLC $t_R$: 1.57 min (method D); TLC $R_f$: 0.36 (5% methanol:methylene chloride).

Example 15

1-Ethyl-2-(4-hydroxy-phenyl)-1,2,3,4-tetrahydro-isoquinolin-6-ol

According to synthetic method G, N-(4-methoxy-phenyl)-N-[2-(3-methoxy-phenyl)-ethyl]-propionamide (0.573 g) was obtained from propionyl chloride (1.2 g). MS: 314.4 (MH$^+$); HPLC $t_R$: 2.78 min; TLC $R_f$: 0.41 (ethyl acetate-hexane 2:3). According to synthetic method H, 1-ethyl-6-methoxy-2-(4-methoxy-phenyl)-1,2,3,4-tetrahydro-isoquinoline was obtained. MS: 298.4 (MH$^+$); HPLC $t_R$: 2.26 min (method D). According to method B, the title compound was obtained (0.053 g) after purification by chromatography on silica gel (eluant: a gradient of 0 to 4% methanol in dichloromethane); MS: 270.4 (MH$^+$); HPLC $t_R$: 1.74 min (method D); TLC $R_f$: 0.41 (5% methanol:methylene chloride).

Example 16

1-Benzyl-2-(4-hydroxy-phenyl)-1,2,3,4-tetrahydro-isoquinolin-6-ol

According to synthetic method G, N-(4-methoxy-phenyl)-N-[2-(3-methroxy-phenyl)-ethyl]-2-phenyl-acetamide (1.19 g) was obtained from phenyl-acetyl chloride (1.14 g). MS: 376.4 (MH$^+$); HPLC $t_R$: 3.03 min; TLC $R_f$: 0.48 (ethyl acetate-hexane 2:3). According to synthetic method H, 1-benzyl-6-methoxy-2-(4-methoxy-phenyl)-1,2,3,4-tetrahydro-isoquinoline was obtained. MS: 360.5 (MH$^+$); HPLC $t_R$: 2.69 min. According to method B, the title compound was obtained (0.609 g) after purification by chromatography on silica gel (eluant: a gradient of 0 to 10% methanol in dichloromethane); MS: 332.4 (MH$^+$); HPLC $t_R$: 2.03 min; TLC $R_f$: 0.6 (5% methanol:methylene chloride).

Example 17

2-(3-Hydroxy-phenyl)-1-methyl-1,2,3,4-tetrahydro-isoquinolin-6-ol

According to synthetic method F, (3-methoxy-phenyl)-[2-(3-methoxy-phenyl)-ethyl]-amine was obtained from 3-methoxy-phenylamine (3.33 g). MS: 258.3 (MH$^+$); HPLC $t_R$: 2.21 min. According to synthetic method G, N-(3-methoxy-phenyl)-N-[2-(3-methoxy-phenyl)-ethyl]-acetamide (0.73 g) was obtained from acetyl chloride (0.53 g). MS: 300.3 (MH$^+$); HPLC $t_R$: 2.51 min (method D); TLC $R_f$: 0.36 (ethyl acetate:hexane-1:1). According to synthetic methods H and B, the title compound (0.184 g) was obtained after purification by chromatography on silica gel (eluant: a gradient of 0 to 5% methanol in dichloromethane); MS: 256.2 (MH$^+$); HPLC $t_R$: 1.44 min (method D); TLC $R_f$: 0.10 (2% methanol:methylene chloride).

Example 18

2-(5-Hydroxy-2-methyl-phenyl)-1-methyl-1,2,3,4-tetrahydro-isoquinolin-6-ol

According to synthetic methods F and G, N-(5-methoxy-2-methyl-phenyl)-N-[2-(3-methoxy-phenyl)-ethyl]-acetamide (0.75 g) was obtained from (3-methoxy-phenyl)-acetyl chloride (4.0 g) and 5-methoxy-2-methyl-phenylamine (2.97 g) followed by reaction with acetyl chloride (1.5 eq). MS: 314.3 (MH$^+$); HPLC $t_R$: 2.63 min (method D); TLC $R_f$: 0.16 (ethyl acetate:hexane-3:7). According to synthetic methods H and B, the title compound (0.026 g) was obtained after purification by chromatography on silica gel (eluant: a gradient of 0 to 50% ethyl acetate in hexane); MS: 270.3 (MH$^+$); HPLC $t_R$: 1.28 min (method D); TLC $R_f$: 0.36 (ethyl acetate:hexane 2:3).

Example 19

2-(3-Chloro-4-hydroxy-phenyl)-1-ethyl-1,2,3,4-tetrahydro-isoquinolin-6-ol

According to synthetic methods F and G, N-(3-chloro-4-methoxy-phenyl)-N-[2-(3-methoxy-phenyl)-ethyl]-propionamide (0.753 g) was obtained from (3-methoxy-phenyl)-acetyl chloride (1.0 eq) and 3-chloro-4-methoxy-phenylamine (1.0 eq) followed by reaction with propionyl chloride (1.5 eq). MS: 348.4 (MH$^+$); HPLC $t_R$: 2.72 mm (method D); TLC $R_f$: 0.48 (ethyl acetate:hexane-1:1). According to synthetic methods H and B, the title compound (0.25 g) was obtained after purification by chromatography on silica gel (eluant: a gradient of 0 to 5% methanol in methylene chloride); MS: 304.2, 306.2 (MH$^+$); HPLC $t_R$: 1.80 min (method D); TLC $R_f$: 0.16 (2% methanol:methylene chloride).

Example 20

2-(3-Hydroxy-4-methyl-phenyl)-1-phenyl-1,2,3,4-tetrahydro-isoquinolin-6-ol

According to synthetic methods F and G, N-(3-methoxy-4-methyl-phenyl)-N-[2-(3-methoxy-phenyl)-ethyl]-benzamide (0.783 g) was obtained from (3-methoxy-phenyl)-acetyl chloride (1.0 eq) and 3-methoxy-4-methyl-phenylamine (1.0 eq) followed by reaction with benzoyl chloride (1.5 eq). MS: 376.3 (MH$^+$); HPLC $t_R$: 2.93 min (method D); TLC $R_f$: 0.45 (ethyl acetate:hexane-3:7). According to synthetic methods H and B, the title compound (0.25 g) was obtained after purification by chromatography on silica gel (eluant: a gradient of 0 to 50% ethyl acetate in hexane); MS: 332.5 (MH$^+$); HPLC $t_R$: 1.89 min (method D); TLC $R_f$: 0.40 (ethyl acetate:hexane 2:3).

Example 21

1-Furan-3-yl-2-(3-hydroxy-4-methyl-phenyl)-1,2,3,4-tetrahydro-isoquinolin-6-ol According to synthetic methods F and G, furan-3-carboxylic acid (3-methoxy-4-methyl-phenyl)-[2-(3-methoxy-phenyl)-ethyl]-amide (0.409 g) was obtained from (3-methoxy-phenyl)-acetyl chloride (1.0 eq) and 3-methoxy-4-methyl-phenylamine (1.0 eq) followed by reaction with furan-3-carbonyl chloride (1.5 eq). MS: 366.3 (MH$^+$); HPLC $t_R$: 2.86 min (method D); TLC $R_f$: 0.44 (ethyl acetate:hexane-3:7). According to synthetic methods H and B, the title compound (0.02 g) was obtained after purification by chromatography on silica gel (eluant: a gradient of 0 to 50% ethyl acetate in hexane); MS: 322.5 (MH$^+$); HPLC $t_R$: 1.71 min (method D); TLC $R_f$: 0.48 (ethyl acetate:hexane 2:3).

Example 22

2-(3-Hydroxy-4-methyl-phenyl)-1-thiophen-2-yl-1,2,3,4-tetrahydro-isoquinolin-6-ol According to synthetic methods F and G, thiophene-2-carboxylic acid (3-methoxy-4-methyl-phenyl)-[2-(3-methoxy-phenyl)-ethyl]-amide (0.583 g) was obtained from (3-methoxy-phenyl)-acetyl chloride (1.0 eq) and 3-methoxy-4methyl-phenylamine (1.0 eq) followed by reaction with thiophene-2-carbonyl chloride (1.5 eq). MS: 382.3 (MH$^+$); HPLC $t_R$: 2.96 min (method D); TLC $R_f$: 0.52 (ethyl acetate:hexane-3:7). According to synthetic methods H and B, the title compound (0.04 g) was obtained after purification by chromatography on silica gel (eluant: a gradient of 0 to 50% ethyl acetate in hexane); MS: 338.5 (MH$^+$); HPLC $t_R$: 2.05 min (method D); TLC $R_f$: 0.44 (ethyl acetate:hexane 2:3).

Example 23

(6-Hydroxy-3,4-dihydro-1H-isoquinolin-2-yl)-(4-hydroxy-phenyl)-methanone

1) Synthetic Method I: (6-methoxy-3,4-dihydro-1H-isoquinolin-2-yl)-(4-methoxy-phenyl)-methanone 4-Methoxy-benzoyl chloride (2.35 g) was added dropwise to a solution of 6-methoxy-1,2,3,4-tetrahydro-isoquinoline (0.75 g) and triethylamine (1.54 mL) in dichloromethane (40 mL) at 0° C. After 18 h at room temperature, the reaction was washed with 1N NaOH (2×50 mL), then water (2×50 mL). The organic extract was dried over sodium sulfate, filtered through celite and concentrated. The (6-methoxy-3,4-dihydro-1H-isoquinolin-2-yl)-(4-methoxy-phenyl)-methanone (0.95 g) product was obtained after purification by chromatography on silica gel (eluant: methylene chloride).

According to synthetic method B, the title compound (0.18 g) was obtained using (6-methoxy-3,4-dihydro-1H-isoquinolin-2-yl)-(4-methoxy-phenyl)-methanone (0.4 g) and after purification by chromatography on silica gel (eluant: 2% methanol:methylene chloride). MS: 270.0 (MH$^+$).

Example 24

(7-Hydroxy-3,4-dihydro-1H-isoquinolin-2-yl)-(4-hydroxy-phenyl)-methanone

According to synthetic method I, (7-methoxy-3,4-dihydro-1H-isoquinolin-2-yl)-(4-methoxy-phenyl)-methanone (0.79 g) was obtained using 7-methoxy-1,2,3,4tetrahydro-isoquinoline (0.75 g). MS: 298.1 MH$^+$. According to synthetic method B, the title compound (0.22 g) was obtained using (7-methoxy-3,4-dihydro-1H-isoquinolin-2-yl)-(4-methoxy-phenyl)-methanone (0.44 g) and after purification by chromatography on silica gel (eluant: tetrahydrofuran:methylene chloride 0:10 to 1:9). MS: 270.2 (MH$^+$).

Isoindolines

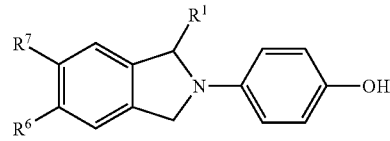

| Example | R$^6$ | R$^7$ | R$^1$ |
|---|---|---|---|
| 25 | H | OH | H |
| 26 | H | OH | Et |
| 27 | H | OH | Ph |
|  | OH | H | Ph |

Example 25

5-Hydroxy-2-(4-hydroxyphenyl)isoindoline

1) Synthesis of 5-hydroxy-2-(4-hydroxyphenyl)isoindoline-1,3-dione

A suspension of 4-hydroxyphthalic acid (3.00 g) and 4-aminophenol (1.98 g) in glacial acetic acid (15 mL) was heated under nitrogen at 120° C. for 1.5 h. The brown reaction solution was cooled to room temperature, poured into water (200 mL) and allowed to sit undisturbed for 30 min. The precipitate was collected by filtration and washed with water (2×60 mL). The solid was dried under high vacuum at 50° C. for 18 h yielding the title compound (3.14 g) as a tan solid. $^1$H NMR (DMSO-d$_6$): 10.99 (s, 1H), 9.72 (s, 1H), 7.76 (d, 1H, J=7.8 Hz), 7.18 (m, 4M), 6.86 (m, 2H); MS: 256 (MH$^+$).

2) Synthesis of 5-benzyloxy-2-(4-benzyloxyphenyl) isoindoline-1,3-dione

To 5-hydroxy-2-(4-hydroxyphenyl)isoindoline-1,3-dione (2.08 g) in DMF (20 mL) was added potassium carbonate (4.62 g) and a solution of benzyl bromide (3.07 g) in DMF (3.0 mL) dropwise under nitrogen atmosphere. The reaction was stirred at room temperature for 2 h then heated to 80° C. for 3 h. The mixture was cooled to room temperature, poured into water (250 mL) and let sit undisturbed for 2.0 h. The white solid was collected by filtration and washed with water. The solid was dried under high vacuum at 50° C. for 18 h yielding the title compound (3.30 g) as a white solid. $^1$H NMR (DMSO-$d_6$): 7.87 (d, 1H, J=8.4 Hz), 7.48-7.35 (m, 12H), 7.32 (d, 2H, J=8.7 Hz), 7.13 (d, 2H, J=8.7 Hz), 5.35 (s, 2H), 5.17 (s, 2H); MS: 436 (MH$^+$).

3) Synthetic Method J: Synthesis of 5-benzyloxy-2-(4-benzyloxyphenyl)isoindoline To a stirred suspension containing LiAlH$_4$ (0.133 g) in THF (10 mL) under nitrogen atmosphere was added 5-benzyloxy-2-(4-benzyloxyphenyl)isoindoline-1,3-dione (0.435 g) in THF (15 mL) dropwise. The reaction was stirred at room temperature for 30 min, poured into cold, saturated ammonium chloride (100 mL) and extracted with ethyl acetate (2×75 mL). The organic layer was washed with brine and dried over MgSO$_4$. After evaporation of the solvent, the residue was dried under high vacuum yielding the title compound (0.4 g) as a brown solid. $^1$H NMR (DMSO-$d_6$): 7.45-7.31 (m, 13H), 6.70 (d, 2H, J=8.5 Hz), 6.51 (d, 2H, J=8.5 Hz), 5.12 (m, 4H), 4.41 (m, 4H); MS: 408 (MH$^+$).

4) Synthetic Method K: Synthesis of 5-hydroxy-2-(4-hydroxyphenyl)isoindoline 5-Benzyloxy-2-(4-benzyloxyphenyl)isoindoline (400 mg) in TFA (12 mL) was refluxed under nitrogen atmosphere for 1 h and cooled. The solvents were removed under vacuum. The residue was dissolved in ethyl acetate (100 mL) and washed with saturated sodium bicarbonate (twice) then brine. Purification by chromatography on silica gel (eluant: dichloromethane—methanol 95:5) gave the title compound (95 mg) as a tan solid. $^1$H NMR (DMSO-$d_6$): 9.35 (s, 1H), 8.53 (s, 1H), 7.14 (d, 1H, J=8.4 Hz), 6.75 (s br, 1H), 6.69 (m, 3H), 6.49 (d, 2H, J=8.7 Hz), 4.38 (m, 4H); MS: 228 (MH$^+$).

Example 26

1-Ethyl-6-hydroxy-2-(4-hydroxyphenyl)isoindoline

1) Synthetic Method L: Synthesis of 5-benzyloxy-2-(4-benzyloxyphenyl)-3-ethyl-3-hydroxyisoindolin-1-one To a cooled (3° C.) solution containing 5-benzyloxy-2-(4-benzyloxyphenyl)-isoindoline-1,3-dione (870 mg) in THF (25 mL) under nitrogen atmosphere was added ethylmagnesium bromide (4 mL, 3M solution in THF) dropwise. The mixture was stirred at 3° C. for 15 min then allowed to warm to room temperature for 2 h. The mixture was cooled, poured into saturated ammonium chloride and extracted with ethyl acetate. The organic layer was washed with brine. Evaporation of the solvent yielded the title compound (900 mg) as a tan solid. MS: 466 (MH$^+$).

2) Synthesis of 6-benzyloxy-2-(4-benzyloxyphenyl)-1-ethylisoindoline

According to synthetic method J except that the mixture was stirred at room temperature for 1 h and at 35° C. for 1 h, from 5-benzyloxy-2-(4-benzyloxyphenyl)-3-ethyl-3-hydroxyisoindolin-1-one (0.5 g) was obtained 6-benzyloxy-2-(4-benzyloxyphenyl)-1-ethylisoindoline (0.5 g). MS: 436 (MH$^+$).

3) Synthesis of 1-ethyl-6-hydroxy-2-(4-hydroxyphenyl)isoindoline

According to synthetic method K, from 6-benzyloxy-2-(4-benzyloxyphenyl)-1-ethylisoindoline (435 mg) was obtained 1-ethyl-6-hydroxy-2-(4-hydroxyphenyl)isoindoline (140 mg). $^1$H NMR (D)MSO-$d_6$): 9.32 (s br, 1H), 8.58 (s br, 1H), 7.31 (d, 1H, J=8.3 Hz), 7.15 (d, 1H, J=8.3 Hz), 6.70 (m, 3H), 6.57 (m, 2H), 4.95 (m, 1H), 4.55 (m, 1H), 4.31 (m, 1H), 1.98 (m, 1H), 1.74 (m, 1H), 0.56 (m, 3H); MS: 256 (MH$^+$).

Example 27

6-Hydroxy-2-(4-hydroxyphenyl)-1-phenylisoindoline and 5-hydroxy-2-(4-hydroxyphenyl)-1-phenylisoindoline

1) Synthesis of 5-benzyloxy-2-(4-benzyloxyphenyl)-3-hydroxy-3-phenylisoindolin-1-one and 6-benzyloxy-2-(4-benzyloxyphenyl)-3-hydroxy-3-phenylisoindolin-1-one According to synthetic method L, from 5-benzyloxy-2-(4-benzyloxyphenyl)-isoindoline-1,3-dione (870 mg) and phenylmagnesium bromide (1M solution in THF, 12 mL) was obtained a mixture of 5-benzyloxy-2-(4-benzyloxyphenyl)-3-hydroxy-3-phenylisoindolin-1-one and 6-benzyloxy-2-(4-benzyloxyphenyl)-3-hydroxy-3-phenylisoindolin-1-one (1.1 g) as a tan foam. MS: 514 (MH$^+$).

2) Synthesis of 6-benzyloxy-2-(4-benzyloxyphenyl)-1-phenylisoindoline and 5-benzyloxy-2-(4-benzyloxyphenyl)-1-phenylisoindoline According to synthetic method J except that the mixture was stirred at room temperature for 1 h and at 35° C. for 1 h, from 5-benzyloxy-2-(4-benzyloxyphenyl)-3-hydroxy-3-phenylisoindolin-1-one (0.53 g) was obtained a mixture of 6-benzyloxy-2-(4-benzyloxyphenyl)-1-phenylisoindoline and 5-benzyloxy-2-(4-benzyloxyphenyl)-1-phenylisoindoline (0.48 g). MS: 484 (MH$^+$).

3) Synthesis of 6-hydroxy-2-(4-hydroxyphenyl)-1-phenylisoindoline and 5-hydroxy-2-(4-hydroxyphenyl)-1-phenylisoindoline According to synthetic method K, from the mixture above (480 mg) was obtained a mixture of 6-hydroxy-2-(4-hydroxyphenyl)-1-phenylisoindoline and 5-hydroxy-2-(4-hydroxyphenyl)-1-phenylisoindoline (85 mg). HPLC (HPLC 2.1× 50 mm C$_8$ 5 μm Zorbax Stablebond column; flow rate 1.4 mL/min, linear gradient from 15% B to 90% B over 4.0 min; A=water, 0.05% TFA; B=90% acetonitrile, 10% water, 0.05% TFA, UV detection at 254 nm and positive ionization mass spectrometry detection) $t_R$: 1.70 min [33%; MS: 304 (MH$^+$)] and 1.83 min [66%; MS: 304 (MH$^+$)].

The invention claimed is:

1. A compound having the formula:

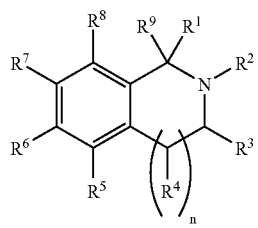

or a pharmaceutically acceptable salt or hydrolyzable ester thereof, wherein:

$R^1$ is H, $C_{1-8}$alkyl, phenyl, or a 5- or 6-membered ring heterocycle containing 1, 2 or 3 heteroatoms each independently selected from O, N and S and additionally having 0 or 1 oxo groups and 0 or 1 fused benzo rings, wherein the $C_{1-8}$alkyl, phenyl or heterocycle is substituted by 0, 1, 2 or 3 substituents selected from —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, $NR^aS(=O)_2R^a$, —$C(=O)R^a$, —$S(=O)R^a$, —$S(=O)_2R^a$, halogen, cyano, nitro and $C_{1-3}$haloalkyl;

$R^2$ is phenyl substituted by 1, 2 or 3 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro and $C_{1-3}$haloalkyl, wherein at least one of the substituents is —OH; and wherein the phenyl is additionally substituted by 0, 1 or 2 substituents selected from $C_{1-6}$alkyl, phenyl and benzyl;

$R^3$ is hydrogen, $C_{1-6}$alkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings;

$R^4$ is H, halogen, $C_{1-6}$alkyl, $C_{1-6}$haloalkyl, —$(CH_2)_m$phenyl or —$(CH_2)_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings;

$R^5$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl; or $R^5$ is $C_{1-3}$alkyl containing 1 or 2 substituents selected from —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano and nitro;

$R^6$ is —OH;

$R^7$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)R^a$, —$S(=O)_2R^a$, halogen, cyano, nitro or $C_{1-3}$haloalkyl;

$R^8$ is —$R^a$, —$OR^a$, —$SR^a$, —$NR^aR^a$, —$CO_2R^a$, —$OC(=O)R^a$, —$C(=O)NR^aR^a$, —$NR^aC(=O)R^a$, —$NR^aS(=O)R^a$, —$NR^aS(=O)_2R^a$, —$C(=O)R^a$, —$S(=O)$ $R^a$, —S(=O)$_2$R$^a$, halogen, cyano, nitro or C$_{1-3}$haloalkyl; or R$^8$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro;

R$^9$ is H, C$_{1-5}$alkyl or C$_{1-3}$haloalkyl;

R$^a$ is H, C$_{1-6}$alkyl, phenyl or benzyl;

m is 0, 1, 2 or 3;

n is 1; and wherein the compound is not 1,2,3,4-tetrahydro-2-(3-hydroxy-4-methoxyphenyl)-7-methoxy-6-isoquinolinol.

2. The compound according to claim 1, wherein R$^1$ is H, phenyl or a 5- or 6-membered ring heterocycle containing 1, 2 or 3 heteroatoms each independently selected from O, N and S and additionally having 0 or 1 oxo groups and 0 or 1 fused benzo rings, wherein the phenyl or heterocycle is substituted by 0, 1, 2 or 3 substituents selected from —R$^a$, —OR$^a$, —SR$^a$, —NR$^a$R$^a$, —OC(=O)R$^a$, —NR$^a$C(=O)R$^a$, —NR$^a$S(=O)R$^a$, —NR$^a$S(=O)$_2$R$^a$, —S(=O)R$^a$, —S(=O)$_2$R$^a$, halogen, cyano, nitro and C$_{1-3}$alkyl substituted with 1-7 halogen atoms.

3. The compound according to claim 1, wherein R$^2$ is phenyl substituted by 1, 2 or 3 substituents selected from —OR$^a$, —SR$^a$, —NR$^a$R$^a$, —OC(=O)R$^a$, —NR$^a$C(=O)R$^a$, —NR$^a$S(=O)R$^a$, —NR$^a$S(=O)$_2$R$^a$, —S(=O)R$^a$, —S(=O)$_2$R$^a$, halogen, cyano, nitro and C$_{1-3}$haloalkyl, wherein at least one of the substituents is —OH; and wherein the phenyl is additionally substituted by 0, 1 or 2 substituents selected from C$_{1-6}$alkyl, phenyl and benzyl.

4. The compound according to claim 1, wherein R$^3$ is C$_{1-6}$alkyl, —(CH$_2$)$_m$phenyl or —(CH$_2$)$_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings.

5. The compound according to claim 1, wherein R$^4$ is halogen, C$_{1-6}$alkyl, C$_{1-6}$haloalkyl, —(CH$_2$)$_m$phenyl or —(CH$_2$)$_m$heterocycle, wherein the heterocycle is a 5- or 6-membered ring heterocycle containing 1, 2 or 3 heteroatoms each independently selected from O, N and S and additionally having 0 or 1 oxo groups and 0 or 1 fused benzo rings.

6. The compound according to claim 1, wherein R$^5$ is C$_{1-6}$alkyl, —OR$^a$, —SR$^a$, —NR$^a$R$^a$, —CO$_2$R$^a$, —OC(=O)R$^a$, —C(=O) NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl; or R$^5$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro.

7. The compound according to claim 1, wherein R$^7$ is —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano, nitro or C$_{1-3}$haloalkyl.

8. The compound according to claim 1, wherein R$^8$ is C$_{1-6}$alkyl, —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, C(=O)R$^a$, —S(=O)R$^a$, —S(=O)$_2$R$^a$, halogen, cyano, nitro or C$_{1-3}$haloalkyl; or R$^8$ is C$_{1-3}$alkyl containing 1 or 2 substituents selected from —OR$^a$, —SR$^a$, —NR$^a$R$^a$, —CO$_2$R$^a$, —OC(=O)R$^a$, —C(=O)NR$^a$R$^a$, —NR$^a$C(=O)R$^a$, —NR$^a$S(=O)R$^a$, —NR$^a$S(=O)$_2$R$^a$, —C(=O)R$^a$, —S(=O)R$^a$, —S(=O)$_2$R$^a$, halogen, cyano and nitro.

9. The compound according to claim 1 wherein:

R$^3$ is H; and

R$^4$ is H.

10. The compound according to any one of claims 1-6, 7, 8 and 9, wherein the compound satisfies the equation:

$(K_{i\alpha A}/K_{i\beta A})/(K_{i\alpha E}/K_{i\beta E}) > 100$, wherein $K_{i\alpha A}$ is the $K_i$ value for the agonist in ER-$\alpha$;

$K_{i\beta A}$ is the $K_i$ value for the agonist in ER-$\beta$;

$K_{i\alpha E}$ is the $K_i$ value for estrogen in ER-$\alpha$; and $K_{i\beta E}$ is the $K_i$ value for estrogen in ER-$\beta$.

11. A method for the treatment of Alzheimer's disease, which comprises administering to a patient in need of such treatment an effective amount of a compound according by any one of claims 1-6, 7, 8 and 9.

12. A pharmaceutical composition comprising:

a therapeutically-effective amount of a compound according to any one of claims 1-6, 7, 8 and 9; and a pharmaceutically-acceptable diluent or carrier.

13. A method for the treatment of Alzheimer's disease, which comprises administering to a patient in need of such treatment an effective amount of a compound according to claim 10.

14. A pharmaceutical composition comprising:

a therapeutically-effective amount of a compound according to claim 10; and a pharmaceutically-acceptable diluent or carrier.

* * * * *

UNITED STATES PATENT AND TRADEMARK OFFICE
CERTIFICATE OF CORRECTION

PATENT NO. : 7,256,201 B2 Page 1 of 1
APPLICATION NO. : 10/450023
DATED : August 14, 2007
INVENTOR(S) : Barlaam et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 268 days Delete the phrase "by 268 days" and insert -- by 329 days --

Signed and Sealed this

Fifteenth Day of April, 2008

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 70
<212> TYPE: DNA
<213> ORGANISM: artificial sequence
<220> FEATURE:
<223> OTHER INFORMATION: Synthetic sequence comprising a
      Vitellogenin-gene Estrogen Response Element
<220> FEATURE:
<221> NAME/KEY: misc_feature
<222> LOCATION: (1)..(5)
<223> OTHER INFORMATION: 5/6 bases from 5' end of cleaved Spe I site
<220> FEATURE:
<221> NAME/KEY: misc_feature
<222> LOCATION: (6)..(11)
<223> OTHER INFORMATION: Xho I site
<220> FEATURE:
<221> NAME/KEY: misc_feature
<222> LOCATION: (27)..(32)
<223> OTHER INFORMATION: Spacer Bgl II site
<220> FEATURE:
<221> NAME/KEY: misc_feature
<222> LOCATION: (70)..(70)
<223> OTHER INFORMATION: 3' overhang C from Afl II cleavage

<400> SEQUENCE: 1
ctagtctcga gaggtcactg tgacctagat ctaggtcact gtgacctaga tctaggtcac    60
tgtgacctac                                                          70
```